United States Patent [19]

Brueckmann et al.

[11] Patent Number: 5,124,438
[45] Date of Patent: Jun. 23, 1992

[54] CHEMICALLY MODIFIED PROTEINS AND COLORANT FORMULATIONS CONTAINING THE SAME

[75] Inventors: Ralf Brueckmann, Goennheim; Johannes P. Dix, Neuhofen; Manfred Herrmann, Ludwigshafen; Herbert Leiter, Maxdorf; Norbert Zimmermann, Waldsee, all of Fed. Rep. of Germany

[73] Assignee: BASF Aktiengesellschaft, Ludwigshafen, Fed. Rep. of Germany

[21] Appl. No.: 464,196

[22] Filed: Jan. 12, 1990

[30] Foreign Application Priority Data

Feb. 4, 1989 [DE] Fed. Rep. of Germany ....... 3903362

[51] Int. Cl.⁵ .......................... C07K 3/08; C08H 1/00; C09B 67/00
[52] U.S. Cl. ........................ 530/354; 8/563; 530/356; 530/360; 530/362; 530/402; 530/408; 530/410
[58] Field of Search .................... 8/563; 530/402, 408, 530/410, 360, 356, 362, 367, 354

[56] References Cited

U.S. PATENT DOCUMENTS

| | | | |
|---|---|---|---|
| 2,304,308 | 12/1942 | Hurd | 530/408 |
| 2,373,602 | 4/1945 | Rust et al. | 530/408 |
| 4,311,480 | 1/1982 | Price et al. | 8/527 |
| 4,494,994 | 1/1985 | Cioca et al. | 530/408 |
| 4,761,161 | 8/1988 | Pötschke | 8/563 |

FOREIGN PATENT DOCUMENTS

| | | | |
|---|---|---|---|
| 71700 | 6/1975 | Japan | 530/408 |
| 213536 | 9/1924 | United Kingdom | 530/402 |
| 2003194 | 3/1979 | United Kingdom | . |

OTHER PUBLICATIONS

Tappi, vol. 58, No. 10, pp. 55–61, Oct. 1975, R. D. Athey, Jr., "Polymeric Organic Dispersants For Pigments: Useful Structures and Their Evaluations".

*Primary Examiner*—Jeffrey E. Russel
*Attorney, Agent, or Firm*—Oblon, Spivak, McClelland, Maier & Neustadt

[57] ABSTRACT

Chemically modified proteins obtainable by reacting casein, collagen, gelatin, albumin or mixtures thereof
  (a) with 0.5 to 15% by weight of chlorine or of a compound which liberates chlorine under the reaction conditions, in an aqueous medium at a pH of from 0 to 7 or
  (b) with 0.5 to 50% by weight of a non-aromatic mono- or disulfonic acid which contains in its organic radical one or more groups or structural features which react with nucleophiles, in an aqueous medium at a pH of from 6 to 14, are used as dispersants in colorant formulations.

16 Claims, No Drawings

CHEMICALLY MODIFIED PROTEINS AND COLORANT FORMULATIONS CONTAINING THE SAME

The present invention relates to novel chemically modified proteins which can be obtained by reacting casein, collagen, gelatin and/or albumin.

(a) with 0.5 to 15% by weight of chlorine or of a compound which liberates chlorine under the reaction conditions, in an aqueous medium at a pH of from 0 to 7 or (b) with 0.5 to 50% by weight of a non-aromatic mono- or disulfonic acid which contains in its organic radical one or more groups or structural features which react with nucleophiles, in an aqueous medium at a pH of from 6 to 14 to a process for the preparation thereof, to the use thereof as dispersants in colorant formulations and to these formulations.

Dispersants conventionally used for colorants, in particular for vat and disperse dyes, are ligninsulfonates, naphthalenesulfonic acid/formaldehyde condensates or sulfonates of phenol/formaldehyde condensates. Normally very few of these are amenable to biological degradation or elimination in clarification plants and they may therefore contribute to pollution of surface waters.

DE-A 27 34 204 describes copolymers of styrene and acrylic acid in the ratio of from 50:50 to 70:30 by weight and of styrene, acrylic acid and maleic anhydride in the ratios from 50:40:10 to 70:24:6 by weight in the form of water-soluble salts as dispersants for dyes. These copolymers are considerably less environmentally polluting than the abovementioned dispersants and, moreover, have an acceptable dispersant action. Nevertheless, the dispersing properties are still in need of further improvement.

Examples of the use of naturally occurring proteins as protective coloids and dispersants have been disclosed. Thus, Athey in Tappi, Vol. 58, No. 10 (1975) 55–61, describes casein, inter alia, as a dispersant for pigments for paper coating. EP-B 018 947 relates to casein in the form of its ammonium salt as an emulsifier in the dyeing of polyester fabric. The naturally occurring proteins and their salts are amenable to virtually complete biological degradation or elimination, but their dispersant properties in respect of colorant formulations are unsatisfactory, especially with regard to dispersion stability.

Hence the object of the present invention was to provide dispersant which, while being amenable to virtually complete biological degradation or elimination, have dispersant properties which meet the high demands of colorant formulations.

In accordance with this, we have found the chemically modified proteins defined in the introduction.

Of the proteins which occur in animal bodies and which can be employed, casein (protein from milk) is particularly important. It is also possible to use collagen (constituent of tendons, ligaments, skin, cartilage and bone) and albumin (protein from eggs). It is likewise possible to use gelatin which is obtained by partial hydrolysis of collagen (gelatin from skin or bone).

Reaction with 0.5 to 15% by weight, preferably 1 to 7% by weight, of chlorine in embodiment (a) is carried out in an aqueous solution or suspension of the protein at a pH of from 0 to 7, preferably 0 to 5. It is usually carried out at from 20° to 100° C., preferably from 50° to 95° C.; however, the reaction can also be carried out above 100° C. under superatmospheric pressure. The acids which are normally employed are strong mineral acids such as hydrochloric acid, sulfuric acid or orthophosphoric acid.

Besides elemental chlorine, it is also possible to employ in embodiment (a) compounds, or mixtures thereof, in an amount of from 0.5 to 15% by weight, preferably 1 to 7% by weight, which liberate chlorine under the reaction conditions. Suitable for this purpose are, for example, alkali metal salts of oxyacids of chlorine, such as hypochlorites or chlorates, in acidic aqueous solution, or peroxo compounds such as hydrogen peroxide, sodium perborate and alkali metal or ammonium salts of peroxomono- and peroxodisulfuric acid in the presence of hydrochloric acid. The pH, the reaction temperature and the choice of acids which can be employed are the same as for the reaction of the proteins with elemental chlorine.

After the proteins have been reacted with chlorine or a compound which liberates chlorine under the reaction conditions, the proteins which have been chemically modified in this way are converted into a form which is adequately soluble in water, preferably by adding a base. The aqueous solutions obtained in this way usually have a pH of from 7 to 10. Bases which can be used are alkali metal or alkaline earth metal oxides or hydroxides, especially sodium or potassium hydroxide, or amines, especially alkanolamines such as mono-, di- or triethanolamine. It is also possible to employ mixtures of the said bases.

The reaction of the proteins with 0.5 to 50% by weight, preferably 1 to 20% by weight, of a non-aromatic mono- or disulfonic acid which contains in its organic radical one or more groups or structural features which react with nucleophiles takes place in embodiment (b) in aqueous solution or suspension at a pH of from 6 to 14, preferably 7 to 12. Examples of suitable groups or structural features which can lead to an attack at nucleophilic reaction centers in the proteins are alkyl radicals, preferably $C_1$–$C_4$-alkyl radicals, which are substituted by hydroxyl groups, which may be sulfated, or chlorine or bromine, as well as the epoxy group and the olefinic double bond, preferably in the $\alpha,\beta$-position. Examples of such mono- and disulfonic acids which may be mentioned are hydroxymethanesulfonic acid, chloromethanesulfonic acid, bromomethanesulfonic acid, vinylsulfonic acid, 2-chloroethanesulfonic acid, 2-bromoethanesulfonic acid, 2-sulfoethyl sulfate, 3-chloro-2-hydroxypropane-1-sulfonic acid, 3-bromo-2-hydroxypropane-1-sulfonic acid, 2,3-epoxypropane-1-sulfonic acid and 1,2-dihydroxyethane-1,2-disulfonic acid. The sulfonic acids are preferably employed as alkali metal, alkaline earth metal, ammonium or amine salts.

Before the reaction with the sulfonic acids as in (b), the proteins are normally dissolved, or at least partially dissolved, with the aid of bases, and the pH is adjusted to the desired range. Bases which can be employed are alkali metal or alkaline earth metal oxides or hydroxides, especially sodium or potassium hydroxide, ammonia or amines, especially alkanolamines such as mono- or di- or triethanolamine. It is also possible to use mixtures of the said bases.

The reaction of the proteins with the sulfonic acids as in (b) is normally carried out at from 20° to 100° C., preferably from 50° to 95° C.; however, the reaction can also be carried out above 100° C. under superatmospheric pressure.

The chemically modified proteins according to the invention can be used in the form of their aqueous solutions, which are usually adjusted to a pH form 7 to 10 after their preparation, and have a low viscosity of, normally, 10 to 200 mPa.s, in a few cases up to 2,500 mPa.s, at 20° C., or in solid form after one of the conventional methods of working up, for example spray drying, freeze drying or evaporation, as dispersants in colorant formulations.

The colorant formulations according to the invention are either anhydrous solids, which are usually in the form of powders, or stable aqueous dispersions. By colorants are meant dyes, for example textile dyes, and pigments. The dyes are usually substances which are sparingly soluble or insoluble in water. The present invention particularly relates to disperse dyes, vat dyes and optical brighteners. The said types of dyes include, in particular, representatives of the classes of azo, anthraquinone and quinophthalone dyes.

The colorant formulations according to the invention contain 0.001 to 10 parts by weight, preferably 0.1 to 2.5 parts by weight, especially 0.7 to 2.2 parts by weight, in the case of solid formulations, and 0.001 to 2 parts by weight, preferably 0.05 to 1.5 parts by weight, especially 0.1 to 0.6 part by weight, in the case of the liquid formulations, of the chemically modified proteins per part by weight of the colorant.

Particularly advantageous colorant formulations are those which, besides the protein derivatives according to the invention, contain copolymers composed of olefinically unsaturated carboxylic acids and/or carboxylic anhydrides on the one hand, and of water-insoluble monomers on the other hand, in the form of water-soluble salts as additional dispersants. These copolymers have been disclosed as dispersants, for example in DE-A 27 34 204. Their dispersant action is based on the principle that they have in the polymer molecule hydrophilic centers such as carboxylate groups in addition to hydrophobic polymer chains.

Particularly suitable copolymers of this type are composed, for example, of
  30 to 50% by weight of acrylic acid and
  50 to 70% by weight of styrene or
  24 to 40% by weight of acrylic acid,
  6 to 10% by weight of maleic anhydride and
  50 to 70% by weight of styrene.

These copolymers can be obtained by conventional methods of free radical polymerization and are employed in a form which has been completely or nearly completely neutralized with alkali metal hydroxides, for example sodium, potassium or lithium hydroxide, ammonia or alkanolamines, for example triethanolamine, tri-n-propanolamine, triisopropanolamine or tetra(hydroxypropyl)ethylenediamine, in aqueous solution.

The colorant formulations according to the invention can contain these water-soluble salts of the copolymers, or mixtures thereof, in an amount of up to 8 parts by weight, preferably up to 2 parts by weight, especially up to 1.1 parts by weight, in the case of the solid formulations, and of up to 1.5 parts by weight, preferably up to 0.5 part by weight, especially up to 0.15 part by weight, in the case of the liquid formulations, per part by weight of the colorant.

The liquid colorant formulations according to the invention contain, besides the colorant and the dispersant, as a rule 20 to 100% by weight, based on the total amount of aqueous dispersion, of water or a mixture of water and water-retaining agents. Water-retaining agents which can be used are ethylene glycol, diethylene glycol, triethylene glycol, propylene glycol, dipropylene glycol, diethylene glycol monobutyl ether, glycerol, sorbitol, dextrin, 2-butyne-1,4-diol or 2-methoxy-1-propanol. Water-retaining agents prevent rapid drying of thin films of the colorant dispersion.

The colorant formulations according to the invention can additionally contain small amounts, up to about 20% by weight based on the total colorant formulation, of the following auxiliaries:

preservatives (biocides) to prevent attack by bacteria and fungi, for example p-chloro-m-cresol, 1,2-benzoisothiazolin-3-one and chloroacetamide pH regulators, especially buffer mixtures containing, for example, alkali metal hydroxides, mono-, di- and triethanolamine, sulfuric acid, hydrochloric acid, phosphoric acid, acetic acid and the alkali metal and ammonium salts of the said acids antifoam agents for suppressing foam when milling the colorant formulations and when using them for dyeing, for example fatty alcohols, fatty alcohol alkoxylates, alkyl esters of carboxylic acids and phosphoric acid, as well as silicone-containing defoamers viscosity regulators to improve the rheological behavior of colorant formulations, for example urea, N-methylacetamide, toluenesulfonates, cumenesulfonates and naphthalenesulfonates to reduce the viscosity and cellulose derivatives and polyacrylates to increase the viscosity wetting agents for improving the redispersibility of colorants in the form of powders and of films, for example alkyl sulfosuccinates, dialkylsulfimides, alkyl phosphates and fatty alcohol alkoxylates dustproofing agents to prevent the formation of dust when handling colorant formulations in the form of powders, especially mixtures of an oily component and of a suitable emulsifier system.

The colorant formulations according to the invention are produced in a conventional manner by milling and dispersing the colorant, as a rule in an aqueous medium, for example in kneaders, ball mills, sand mills, bead mills or attritors. The colorant can be employed for this in the form of a dry powder or, preferably, in the form of the water-containing press cake produced in the preparation of the colorant. To produce the colorant formulations in the form of a powder according to the invention, the resulting aqueous colorant dispersion is, as a rule, spray-dried in a conventional manner, for example at from 60° to 160° C.

The colorant formulations according to the invention are suitable for all dyeing and printing processes.

The chemically modified proteins according to the invention, as well as the copolymers which are to be used in combination with them and which are composed of, for example, styrene, acrylic acid and maleic anhydride, are amenable to virtually complete biological degradation or elimination and thus do not pollute the environment. The biodegradability in the Zahn-Wellens test, defined by determining the chemical oxygen demand during the degradation process, is usually greater than 90% for both classes of substances. By contrast, the ligninsulfonates, naphthalenesulfonic acid/formaldehyde condensates and sulfonates of phenol/formaldehyde condensates which are conventionally used as dispersants for colorant formations mostly have degradabilities below 40%.

The chemically modified proteins according to the invention have a powerful dispersant action. The colorant dispersions produced with them are very finely divided and, at the same time, stable. The colorant formulations according to the invention have high thermal stability, i.e. the colorant dispersions are very stable under the conditions in the hot dyeing liquors. In addition, formulations in the form of powders and colorant films are highly dispersible.

Another advantage of the chemically modified proteins according to the invention is their light color. Thus, when they are used as dispersants in colorant formations, there is no longer a risk that adjacent fabrics are stained during the dyeing of textiles. This is important in the case of brilliant color shades and, especially, when treating textiles with optical brighteners.

Combination of the chemically modified proteins according to the invention with, for example, the copolymers of styrene and acrylic acid, with or without maleic anhydride, disclosed in DE-A 27 34 204 results in a further distinct improvement in the dispersing power. This is shown, especially, by the greater thermal stability and the longer shelf-life of these formulations. An additional advantage of this connection is the low tendency for dyes to migrate in continuous dyeing processes, i.e. the colors have a greater levelness.

Unless stated otherwise, the percentages in the examples relate to weight. The viscosities were measured in a rotary viscometer (Haake, Rotavisco) at 20° C.

The biodegradability was determined by the Zahn-Wellens test described in DIN 38412 part 25. This test makes use of an activated sludge with a mixture of various microorganisms and mineral nutrients for the biodegradation of the test substance. The aqueous solution of these three components was aerated for a defined time (up to 28 days) at a constant temperature of about 22° C. with substantial exclusion of light. The decrease in the amount of test substance was measured by determining the chemical oxygen demand.

The degradability measured in this way was 38% for a commercial naphthalenesulfonic acid/formaldehyde condensate and 33% for a ligninsulfonate.

PREPARATION EXAMPLES

EXAMPLE 1

Reaction of casein with chlorine in hydrochloric acid 300 g of casein were introduced a little at a time into a mixture of 1,000 g of water and 90 g of 36% strength hydrochloric acid at 65° C. The suspension was stirred at 85° to 90° C. for 3 hours. Subsequently, at 60° C. and a pH of 0 to 1, 8.0 g of gaseous chlorine (corresponding to 2.7% based on casein) were passed in within 45 minutes. The suspension was then stirred at 60° C. for 20 minutes and 70° C. for 20 minutes. After it had been cooled to room temperature, 98 g of 50% strength sodium hydroxide solution were added to produce a clear solution with a pH of 7.5 and a viscosity of 18 mPa.s. The biodegradability was 96%.

EXAMPLE 2

Reaction of casein with sodium hypochlorite in sulfuric acid 300 g of casein were introduced a little at a time into a mixture of 1,500 g of water and 45 g of 96% strength sulfuric acid at 60° C. The suspension was stirred at this temperature for 2 hours. Subsequently, at a pH of 0 to 1, 60 g of an aqueous sodium hypochlorite solution which contained 14% active chlorine (corresponding to at least 5.9% NaOCl based on casein) were added dropwise at 60° to 70° C. within 30 minutes. The suspension was then stirred at 80° C. for 2 hours. After cooling to room temperature, 100 g of 50% strength sodium hydroxide solution were added to adjust to a pH of 8.5. The resulting clear solution had a viscosity of 25 mPa.s.

EXAMPLE 3

Reaction of casein with sodium chlorate in hydrochloric acid 200 g of casein were introduced a little at a time into a mixture of 915 g of water and 85 g of 36% strength hydrochloric acid at 65° to 70° C. The suspension was stirred at 80° C. for 3 hours and then, at a pH of 0 to 1, a solution of 2.6 g of sodium chlorate (corresponding to 1.3% based on casein) and 0.1 g of iron(III) chloride hexahydrate in 4 g of water was added all at once, and the mixture was stirred at 70° C. for 2 hours and then at 85° C. for 2 hours. After it had been cooled to room temperature, 92 g of 50% strength sodium hydroxide solution were added to produce a clear solution with a pH of 8.5 and a viscosity of 12 mPa.s

EXAMPLE 4

Reaction of casein with sodium chlorate in sulfuric acid 200 g of casein were introduced a little at a time into a mixture of 1,000 g of water and 30 g of 96% strength sulfuric acid at 60° C. The suspension was stirred at 60° to 65° C. for 2 hours and then, at a pH of 0 to 1, 0.1 g of iron(III) chloride hexahydrate and then 2.6 g of sodium chlorate (corresponding to 1.3% based on casein) dissolved in 4 g of water were added dropwise, and the mixture was stirred at 70° to 75° C. for 2 hours and at 90° to 95° C. for 4 hours. After if had cooled to room temperature, 59 g of 50% strength sodium hydroxide solution was added to adjust to a pH of 8.5. The resulting solution had a viscosity of 180 mPa.s. The biodegradability was 94%.

EXAMPLE 5

Reaction of casein with hydrogen peroxide in hydrochloric acid 200 g of casein were introduced a little at a time into a mixture of 1,000 g of water and 60 g of 36% strength hydrochloric acid at 60° to 65° C. The suspension was stirred at this temperature for 2 hours. Subsequently, at 70° C. and a pH of 0 to 1, 8.3 g of 30% strength hydrogen peroxide (corresponding to 1.2% anhydrous reagent based on casein) were added dropwise within 20 minutes. The suspension was then stirred at 70° C. for a further 2 hours. After the mixture had been cooled to room temperature, 69 g of 50% strength sodium hydroxide solution were added to produce a clear solution with a pH of 8.5 and a viscosity of 27 mPa.s. The biodegradability was 95%.

EXAMPLE 6

Reaction of casein with sodium hydroxymethanesulfonate in sodium hydroxide solution 300 g of casein were introduced a little at a time into a mixture of 1,500 g of water and 54 g of 50% strength sodium hydroxide solution at 60° C. and were substantially dissolved by stirring at this temperature for one hour. To this solution, which had a pH of 10.5, were added dropwise, at the same temperature, 182 g of a 33% strength aqueous sodium hydroxymethanesulfonate solution (corresponding to 20.0% anhydrous reagent based on casein) within 30 minutes. The reaction mixture was then stirred at 90° C. for 3 hours. The resulting solution had a pH of 9.5 and a viscosity of 21 mPa.s. The biodegradability was 93%.

EXAMPLE 7

Reaction of casein with sodium vinylsulfonate in sodium hydroxide solution 1,300 g of casein were introduced a little at a time into a mixture of 3,500 g of water and 252 g of 50% strength sodium hydroxide solution at 60° C. and were substantially dissolved by stirring at this temperature for one hour. To this solution, which had a pH of 8.5, were added dropwise, at the same temperature, 520 g of a 25% strength aqueous sodium vinylsulfonate solution (corresponding to 10.0% anhydrous reagent based on casein) within 1 hour. The reaction mixture was then stirred at 90° C. for 8 hours. After it had been cooled to room temperature, 45 g of 36% strength hydrochloric acid were added to adjust to a pH of 9. The resulting clear solution had a viscosity of 24 mPa.s. The biodegradability was 90%.

EXAMPLE 8

Reaction of casein with sodium 3-chloro-2-hydroxypropane-1-sulfonate in sodium hydroxide solution 200 g of casein were introduced a little at a time into a mixture of 1,000 g of water and 36 g of 50% strength sodium hydroxide solution at 60° C. and were substantially dissolved by stirring at this temperature for one hour. The pH was then adjusted to 10 with 50% strength sodium hydroxide solution. To this solution were added at 60° C. 10 g of sodium 3-chloro-2-hydroxypropane-1-sulfonate (corresponding to 5.0% based on casein). The reaction mixture was then stirred at 80° C. for 2 hours. The resulting clear solution had a pH of 11 and a viscosity of 15 mPa.s.

EXAMPLE 9

Reaction of casein with disodium 1,2-dihydroxyethane-1,2-disulfonate in sodium hydroxide solution 200 g of casein were introduced a little at a time into a mixture of 1,000 g of water and 36 g of 50% strength sodium hydroxide solution at 60° C. and were substantially dissolved by stirring at this temperature for one hour. To this solution, which had a pH of 8.7, were added dropwise, at the same temperature, 153 g of a 16% strength aqueous solution of disodium 1,2-dihydroxyethane-1,2-disulfonate (corresponding to 12.2% anhydrous reagent based on casein) within 0.7 hours. The reaction mixture was then stirred at 90° C. for 3 hours. After it had been cooled to room temperature, the pH was adjusted to 8 with a little 50% strength sodium hydroxide solution. The resulting clear solution had a viscosity of 2,100 mPa.s. The biodegradability was 94%.

EXAMPLES 10 TO 14

Copolymers of styrene, acrylic acid and maleic anhydride

Copolymers of styrene and acrylic acid (Example 10) and styrene, acrylic acid and maleic anhydride (Examples 11 to 14) were prepared as specified in DE-A 27 34 204. The terpolymer had a biodegradability of 95%. The copolymer was converted into a water-soluble salt by reaction with each of the bases mentioned in Table 1 in an aqueous medium at about 60° C. The degree of neutralization was 100 mol-% in each case. These solutions had a solids content of from 20 to 40% and were used as additional dispersants for colorant formulations.

TABLE 1

| | Neutralized copolymers | | | |
| | Composition (%) | | | |
| Example No. | Styrene | Acrylic acid | Maleic anhydride | Base |
|---|---|---|---|---|
| 10 | 70 | 30 | | triethanolamine |
| 11 | 60 | 30 | 10 | triethanolamine |
| 12 | 60 | 30 | 10 | tetra(hydroxypropyl)-ethylenediamine |
| 13 | 60 | 30 | 10 | sodium hydroxide |
| 14 | 60 | 30 | 10 | lithium hydroxide |

USE EXAMPLES

The particle distribution in the colorant dispersions was characterized by the method of Richter and Vescia, Melliand Textilberichte (1965), No. 6, pages 621–625. The numbers correspond to the percentages of colorant which sediment on centrifugation at 1,000, 2,000 and 4,000 rpm after 5 minutes (first 3 numbers) and which remain in the dispersion at the end (4th number). Colorants with small sedimentation percentages and a high final percentage are particularly finely divided.

The sedimentation percentages from comparative tests with commercial naphthalenesulfonic acid/formaldehyde condensate and ligninsulfonate are included in Tables 2 and 3 (Examples 46 to 51 and 66 to 70).

EXAMPLES 15 TO 45 AND COMPARATIVE EXAMPLES 46 TO 51

Liquid colorant formulations

The amounts specified in Table 2, in each case based on the anhydrous substance, unless otherwise indicated, of colorant, which was employed in the form of a press cake moist with water, and of dispersants and auxiliaries were made into a paste by vigorously stirring with water, with the total amount of the mixture being 1,000 g in each case. The mixture was then milled under the conditions specified in Table 2 (bead milling: duration; sand milling: number of millings in which the mixture takes about 45 minutes to pass through the mill) until a satisfactorily fine distribution, characterized by the sedimentation percentages, is achieved. The pH of the dispersions was adjusted to the indicated value in each case by adding acetic acid or sodium hydroxide solution and was maintained during the milling.

EXAMPLES 52 TO 65 AND COMPARATIVE EXAMPLES 66 TO 60

Solid colorant formulations

The amounts specified in Table 3, in each case based on the anhydrous substance, unless indicated otherwise, of colorant, which was employed in the form of a press cake moist with water, and of dispersants and, where appropriate, auxiliaries were made into a paste by vigorously stirring with about 25% (Examples 52-55 and 66), about 60% (Examples 59-62, 68 and 69) or 100 (Examples 56-58, 63-65, 67 and 70) of the total amount of water required, where the amount of water required was calculated on the basis of the solids content of the dispersion before spray drying. The mixture was then milled at a pH of 8 to 9 in the case of colorants J and K or 10 to 11 in the case of colorants F, G and H under the conditions specified in Table 3 (bead milling: duration; sand milling: number of millings with the mixture taking about 45 minutes to pass through the mill) until a satisfactorily fine distribution was achieved.

Subsequently, where appropriate, further amounts of dispersant and the remaining water were added. These dispersions were spray-dried at the temperature indicated in Table 3 in each case. The percentage compositions of the colorant formulations are indicated in Table 3. The sedimentation percentages were determined after the resulting formulations in the form of powders had been resuspended in water.

TABLE 2

Liquid colorant formulations

| Example No. | Colorant | Amount [g] | Dispersant from Example No. | Amount [g] | Auxiliary | Amount [g] | Type and duration of milling [h] | pH | Sedimentation percentages |
|---|---|---|---|---|---|---|---|---|---|
| 15 | A | 220 | 6 | 80 | L | 150 | 5 P | 8-8,5 | 6/13/33/48 |
|   |   |   |   |   | M | 10 |   |   |   |
| 16 | A | 220 | 7 | 80 | L | 150 | 6 P | 8-8,5 | 4/16/28/52 |
|   |   |   |   |   | M | 10 |   |   |   |
| 17 | A | 220 | 2 | 80 | L | 150 | 5 P | 8-8,5 | 1/17/32/50 |
|   |   |   |   |   | M | 10 |   |   |   |
| 18 | B | 250 | 2 | 80 | L | 50 | 7 P | 8-8,5 | 5/12/37/46 |
|   |   |   |   |   | M | 10 |   |   |   |
|   |   |   |   |   | N | 50 |   |   |   |
| 19 | B | 250 | 7 | 130 | L | 50 | 7 P | 8-8,5 | 2/21/19/58 |
|   |   |   |   |   | M | 10 |   |   |   |
|   |   |   |   |   | N | 50 |   |   |   |
| 20 | B | 250 | 6 | 80 | L | 50 | 7 P | 8-8,5 | 8/17/22/53 |
|   |   |   |   |   | M | 10 |   |   |   |
|   |   |   |   |   | N | 50 |   |   |   |
| 21 | C | 170 | 7 | 80 | L | 100 | 6 P | 8-8,5 | 7/12/20/61 |
|   |   |   |   |   | M | 10 |   |   |   |
| 22 | C | 170 | 6 | 80 | L | 100 | 5 P | 8-8,5 | 9/16/24/51 |
|   |   |   |   |   | M | 10 |   |   |   |
| 23 | C | 170 | 2 | 80 | L | 100 | 6 P | 8-8,5 | 11/19/25/45 |
|   |   |   |   |   | M | 10 |   |   |   |
| 24 | D | 200 | 7 | 80 | M | 10 | 2 P | 8-8,5 | 3/6/22//69 |
|   |   |   |   |   | N | 100 |   |   |   |
|   |   |   |   |   | Q | 50 |   |   |   |
| 25 | D | 200 | 2 | 80 | M | 10 | 3 P | 8-8,5 | 2/7/19/72 |
|   |   |   |   |   | N | 100 |   |   |   |
|   |   |   |   |   | Q | 50 |   |   |   |
| 26 | D | 200 | 6 | 80 | M | 10 | 2 P | 8-8,5 | 1/9/25/65 |
|   |   |   |   |   | N | 100 |   |   |   |
|   |   |   |   |   | Q | 50 |   |   |   |
| 27 | D | 200 | 4 | 80 | M | 10 | 2 P | 8-8,5 | 4/10/22/64 |
|   |   |   |   |   | N | 100 |   |   |   |
|   |   |   |   |   | Q | 50 |   |   |   |
| 28 | D | 200 | 5 | 80 | M | 10 | 2 P | 8-8,5 | 5/9/19/67 |
|   |   |   |   |   | N | 100 |   |   |   |
|   |   |   |   |   | Q | 50 |   |   |   |
| 29 | D | 200 | 1 | 80 | M | 10 | 2 P | 8-8,5 | 2/10/20/68 |
|   |   |   |   |   | N | 100 |   |   |   |
|   |   |   |   |   | Q | 50 |   |   |   |
| 30 | D | 200 | 9 | 80 | M | 10 | 2 P | 8-8,5 | 5/12/19/64 |
|   |   |   |   |   | N | 100 |   |   |   |
|   |   |   |   |   | Q | 50 |   |   |   |
| 31 | E | 250 | 2 | 80 | R | 150 | 16 P | 8,5-9 | 9/16/28/47 |
|   |   |   |   |   | T | 150 |   |   |   |
| 32 | E | 250 | 6 | 80 | R | 150 | 16 P | 8,5-9 | 13/13/31/33 |
|   |   |   |   |   | T | 150 |   |   |   |
| 33 | E | 250 | 7 | 80 | R | 150 | 16 P | 8,5-9 | 12/23/32/33 |
|   |   |   |   |   | T | 150 |   |   |   |
| 34 | F | 190 | 2 | 30 | L | 200 | 6 P | 10-11 | 1/2/14/83 |
|   |   |   | 10 | 20 | M | 10 |   |   |   |
| 35 | F | 190 | 2 | 30 | L | 200 | 6 P | 10-11 | 2/5/18/75 |
|   |   |   | 11 | 20 | M | 10 |   |   |   |
| 36 | F | 190 | 2 | 30 | L | 200 | 6 P | 10-11 | 1/3/10/86 |
|   |   |   | 12 | 20 | M | 10 |   |   |   |
| 37 | G | 210 | 2 | 20 | M | 10 | 3 × S | 10-11 | 2/7/11/80 |
|   |   |   | 10 | 20 | N | 180 |   |   |   |
| 38 | G | 210 | 2 | 50 | M | 10 | 5 × S | 10-11 | 1/4/7/88 |
|   |   |   |   |   | N | 180 |   |   |   |
| 39 | H | 230 | 2 | 30 | L | 200 | 6 P | 10-11 | 5/18/28/49 |

TABLE 2-continued

Liquid colorant formulations

| Example No. | Colorant | Amount [g] | Dispersant from Example No. | Amount [g] | Auxiliary | Amount [g] | Type and duration of milling [h] | pH | Sedimentation percentages |
|---|---|---|---|---|---|---|---|---|---|
| 40 | H | 230 | 10 | 20 | M | 10 | 6 P | 10-11 | 4/24/31/41 |
|   |   |     | 2  | 30 | L | 200 |    |       |            |
| 41 | H | 230 | 11 | 20 | M | 10 | 3 × S | 10-11 | 5/17/29/49 |
|   |   |     | 2  | 70 | L | 200 |    |       |            |
| 42 | H | 230 | 6  | 70 | M | 10 | 4 × S | 10-11 | 4/22/30/44 |
|   |   |     |    |    | L | 200 |    |       |            |
| 43 | H | 230 | 4  | 70 | M | 10 | 8 P | 10-11 | 7/8/29/56 |
|   |   |     |    |    | L | 200 |    |       |            |
| 44 | H | 230 | 5  | 50 | M | 10 | 6 P | 10-11 | 6/12/30/52 |
|   |   |     |    |    | L | 200 |    |       |            |
| 45 | H | 230 | 9  | 50 | M | 10 | 6 P | 10-11 | 2/22/33/43 |
|   |   |     |    |    | L | 200 |    |       |            |
| 46 | A | 220 | Y  | 120 | M | 10 | 5 P | 8-8,5 | 2/10/31/52 |
|   |   |     |    |    | L | 150 |    |       |            |
| 47 | C | 170 | Y  | 80 | M | 10 | 6 P | 8-8,5 | 8/16/29/47 |
|   |   |     |    |    | L | 100 |    |       |            |
| 48 | D | 200 | Y  | 100 | M | 10 | 2 P | 8-8,5 | 6/17/30/47 |
|   |   |     |    |    | N | 100 |    |       |            |
|   |   |     |    |    | Q | 50  |    |       |            |
| 49 | F | 190 | X  | 40 | L | 200 | 6 P | 10-11 | 2/5/27/66 |
|   |   |     |    |    | M | 10  |    |       |            |
| 50 | G | 210 | Y  | 50 | M | 10 | 5 × S | 10-11 | 2/7/34/57 |
|   |   |     |    |    | N | 180 |    |       |            |
| 51 | H | 230 | Y  | 110 | L | 200 | 6 P | 10-11 | 5/15/33/47 |
|   |   |     |    |    | M | 10  |    |       |            |

TABLE 3

Solid colorant formulations

| Example No. | Colorant | | Dispersant from Example No./Auxiliary Amount | | | | | Type and duration of milling | | Solids content of the dispersion before spray drying [%] | Temperature during spray-drying [°C.] | Sedimentation percentages |
|---|---|---|---|---|---|---|---|---|---|---|---|---|
| | | | | before/after milling | | total | | | | | | |
| | Amount [g] | [%] | | [g] | [g] | [g] | [%] | [h] | [%] | | | |
| 52 | J | 300 | 40 | 2 | 200 | 250 | 450 | 60 | 3 × S | 25 | 100 | 4/11/28/57 |
| 53 | J | 300 | 40 | 6 | 200 | 250 | 450 | 60 | 4 × S | 25 | 90 | 4/14/32/60 |
| 54 | J | 300 | 40 | 7 | 200 | 250 | 450 | 60 | 3 × S | 25 | 100 | 5/12/24/59 |
| 55 | J | 300 | 40 | 7 | 160 | 200 | 360 | 48 | 5 × S | 25 | 110 | 4/11/18/67 |
|    |   |     |    | 10 | 40 | 50 | 90 | 12 |      |    |     |           |
| 56 | K | 200 | 32 | 6 | 150 | 62,5 | 212,5 | 34 | 3 P | 29 | 100 | 5/9/20/66 |
|    |   |     |    | 10 | 150 | 62,5 | 212,5 | 34 |     |    |     |           |
| 57 | K | 200 | 32 | 2 | 300 | 125 | 425 | 68 | 3 P | 29 | 100 | 4/4/16/76 |
| 58 | K | 200 | 32 | 7 | 300 | 125 | 425 | 68 | 3 P | 29 | 100 | 9/17/21/53 |
| 59 | F | 190 | 36,5 | 7 | 36 | 162 | 198 | 38 | 4 P | 17 | 130 | 2/5/11/82 |
|    |   |     |      | 13 | 24 | 108 | 132 | 25,5 |   |    |     |           |
| 60 | F | 190 | 36,5 | 7 | 60 | 270 | 330 | 63,5 | 6 P | 17 | 130 | 2/6/8/84 |
| 61 | G | 265 | 40,6 | 7 | 135 | 96 | 231 | 35,3 | 4 P | 32 | 130 | 3/8/10/79 |
|    |   |     |      | 13 | 90 | 64 | 154 | 23,6 |   |    |     |           |
|    |   |     |      | U | 3,5 | — | 3,5 | 0,5 |    |    |     |           |
| 62 | G | 265 | 40,6 | 7 | 225 | 160 | 385 | 58,9 | 4 P | 32 | 130 | 3/7/10/80 |
|    |   |     |      | U | 3,5 | — | 3,5 | 0,5 |    |    |     |           |
| 63 | H | 230 | 46 | 2 | 162 | — | 162 | 32,4 | 6 P | 20 | 130 | 4/19/27/50 |
|    |   |     |    | 13 | 108 | — | 108 | 21,6 |    |    |     |           |
| 64 | H | 230 | 46 | 2 | 162 | — | 162 | 32,4 | 6 P | 20 | 130 | 6/19/27/48 |
|    |   |     |    | 14 | 108 | — | 108 | 21,6 |    |    |     |           |
| 65 | H | 230 | 46 | 2 | 270 | — | 270 | 54 | 3 × S | 20 | 130 | 5/16/28/51 |
| 66 | J | 300 | 40 | Y | 200 | 250 | 450 | 60 | 4 × S | 25 | 100 | 2/12/25/61 |
| 67 | K | 200 | 40 | Y | 150 | 150 | 300 | 60 | 3 P | 30 | 100 | 4/13/31/52 |
| 68 | F | 190 | 36,5 | Y | 60 | 270 | 330 | 63,5 | 6 P | 17 | 130 | 1/6/20/73 |
| 69 | G | 265 | 40,6 | X | 190 | 135 | 325 | 49,7 | 4 P | 32 | 130 | 1/4/17/78 |
|    |   |     |      | Y | 35 | 25 | 60 | 9,2 |    |    |     |           |
|    |   |     |      | U | 35 | — | 35 | 0,5 |    |    |     |           |
| 70 | H | 230 | 46 | X | 195 | — | 195 | 39 | 3 × S | 20 | 130 | 6/16/32/46 |

TABLE 3-continued

Solid colorant formulations

| Example No. | Colorant | | Dispersant from Example No./Auxiliary Amount | | | | Type and duration of milling | | Solids content of the dispersion before spray drying [%] | Temperature during spray-drying [°C.] | Sedimentation percentages |
|---|---|---|---|---|---|---|---|---|---|---|---|
| | Amount [g] | [%] | before/after milling [g] | [g] | total [g] | [%] | [h] | [%] | | | |
| | | | Y | 75 | — | 75 | 15 | | | | | meanings of abbreviations in Tables 2 and 3
The colorants employed are the following dyes listed in the Color Index:
A = Disperse Blue 60, C.I. 61100 (anthraquinone dye)
B = Disperse Red 91 (anthraquinone dye)
C = Disperse Yellow 64, C.I. 47023 (hydroxyquinophthalone dye)
D = Disperse Blue 79, C.I. 11345 (azo dye)
E = Fluorescent Brightening Agent 199 (terephthalic acid derivative)
F = Vat Blue 4, C.I. 69800 (anthraquinone dye)
G = Vat Blue 6, C.I. 69825 (anthraquinone dye)
H = Vat Green 1, C.I. 59825 (anthraquinone dye)
J = Disperse Blue 330 (azo dye)
K = Disperse Red 167:1 (azo dye)
The following auxiliaries were also used:
L = glycerol (as water-retaining agent)
M = 1,2-benzoisothiazolin-3-one (as biocide) in the form of a 9.5% strength solution in water/propylene glycol
N = sorbitol (as water-retaining agent)
Q = propylene glycol (as water-retaining agent)
R = ethylene glycol (as water-retaining agent)
T = triethanolamine (as pH regulator)
U = sodium salt of di-$C_9$—$C_{11}$-alkylsulfimide (as wetting agent)
The following types of milling were used:
P = bead milling
S = sand milling
The following commercial dispersants were used for the comparative examples:
X = naphthalenesulfonic acid/formaldehyde condensate (in the form of the sodium salt)
Y = ligninsulfonate (in the form of the sodium salt)

We claim:

1. A chemically modified protein obtained by reacting casein, collagen, gelatin, albumin or mixtures thereof
   (a) with 0.5 to 15% by weight of chlorine or of a compound which liberates chlorine under the reaction conditions, in an aqueous medium at a pH of from 0 to 7 and at a temperature of from 50° to 95° C.; or
   (b) with 0.5 to 50% by weight of a non-aromatic mono- or disulfonic acid or salt thereof which contains an organic radical with one or more groups or structural features, which react with nucleophiles, selected from the group consisting of $C_{1-4}$-alkyl or alkylene radicals which are substituted with hydroxyl groups, $C_{1-4}$-alkyl or alkylene radicals which are substituted with sulfated hydroxyl groups, $C_{1-4}$-alkyl or alkylene radicals which are substituted with chlorine, $C_{1-4}$-alkyl or alkylene radicals which are substituted with bromine, $C_{1-4}$-alkyl or alkylene radicals which are substituted with an epoxy group, and $C_{1-4}$ alkenyl or alkenylene radicals which contain an α-β-double bond, in an aqueous medium at a pH of from 6 to 14.

2. A chemically modified protein as claimed in claim 1, obtainable by reaction of casein.

3. A chemically modified protein as claimed in claim 1, obtainable by reaction in method (a) with 1 to 7% by weight of chlorine or of a compound which liberates chlorine under the reaction conditions.

4. A chemically modified protein as claimed in claim 1, obtainable by reaction in method (a) at a pH of from 0 to 5.

5. A chemically modified protein as claimed in claim 1, obtainable by reaction in method (b) with 1 to 20% by weight of a non-aromatic mono- or disulfonic acid which contains in its organic radical one or more groups or structural features which react with nucleophiles.

6. A chemically modified protein as claimed in claim 1, obtainable by reaction in method (b) at a pH of from 7 to 12.

7. The modified protein of claim 1, wherein said non-aromatic mono- or disulfonic acid or salt thereof is selected from the group consisting of hydroxymethanesulfonic acid, chloromethanesulfonic acid, bromomethanesulfonic acid, vinylsulfonic acid, 2-chloroethanesulfonic acid, 2-bromoethanesulfonic acid, 2-sulfoethyl sulfate, 3-chloro-2-hydroxypropane-1-sulfonic acid, 3-bromo-2-hydroxypropane-1-sulfonic acid, 2,3-epoxypropane-1-sulfonic acid and 1,2-dihydroxyethane-1,2-disulfonic acid.

8. The modified protein of claim 1, wherein said non-aromatic mono- or disulfonic acid or salt thereof is an alkali metal, alkaline earth metal, ammonium or amine salt.

9. A process for the preparation of a chemically modified protein which comprises reacting casein, collagen, gelatin, albumin or mixtures thereof
   (a) with 0.5 to 15% by weight of chlorine or of a compound which liberates chlorine under the reaction conditions, in an aqueous medium at a pH of from 0 to 7 and at a temperature of from 50° to 95° C.; or
   (b) with 0.5 to 50% by weight of a non-aromatic mono- or disulfonic acid or salt thereof which contains an organic radical with one or more groups or structural features, which react with nucleophiles, selected from the group consisting of $C_{1-4}$-alkyl or alkylene radicals which are substituted with hydroxyl groups, $C_{1-4}$-alkyl or alkylene radicals which are substituted with sulfated hydroxyl groups, $C_{1-4}$-alkyl or alkylene radicals which are substituted with chlorine, $C_{1-4}$-alkyl or alkylene radicals which are substituted with bromine, $C_{1-4}$-alkyl or alkylene radicals which are substituted with an epoxy group, and $C_{1-4}$ alkenyl or alkenylene radicals which contain an α-β-double bond, in an aqueous medium at a pH of from 6 to 14.

10. The modified protein of claim 1, wherein said non-aromatic mono- or disulfonic acid or salt thereof is selected from the group consisting of hydroxymethanesulfonic acid, chloromethanesulfonic acid, bromomethanesulfonic acid, vinylsulfonic acid, 2-chloroethanesulfonic acid, 2-bromoethanesulfonic acid, 2-sulfoethyl sulfate, 3-chloro-2-hydroxypropane-1-sulfonic acid, 3-bromo-2-hydroxypropane-1-sulfonic acid, 2,3-epoxypropane-1-sulfonic acid and 1,2-dihydroxyethane-1,2-disulfonic acid.

11. The process of claim 9, wherein said non-aromatic mono- or disulfonic acid or salt thereof is an alkali metal, alkaline earth metal, ammonium or amine salt.

12. A process for the dispersion of colorants in colorant formulations, which comprises using for this purpose a chemically modified protein as claimed in claim 1.

13. A solid anhydrous or liquid aqueous colorant formulation containing as dispersant a chemically modified protein as claimed in claim 1.

14. A solid anhydrous colorant formulation as claimed in claim 13, containing 0.001 to 10 parts by weight of the dispersant per part by weight of the colorant.

15. A liquid aqueous colorant formulation as claimed in claim 13, containing 0.001 to 2 parts by weight of the dispersant per part by weight of the colorant.

16. A colorant formulation as claimed in claim 13, containing as additional dispersant water-soluble salts of copolymers composed of olefinically unsaturated carboxylic acids, carboxylic anhydrides or mixtures thereof on the one hand, and of water-insoluble monomers on the other hand.

* * * * *